(12) United States Patent
Sanders, Jr.

(10) Patent No.: US 9,730,696 B2
(45) Date of Patent: Aug. 15, 2017

(54) SURGICAL PIN COMPRESSION WOUND DRESSING DEVICE

(76) Inventor: Stephen Michael Sanders, Jr., Port Saint Lucie, FL (US)

( * ) Notice: Subject to any disclaimer, the term of this patent is extended or adjusted under 35 U.S.C. 154(b) by 0 days.

(21) Appl. No.: 13/066,719

(22) Filed: Apr. 23, 2011

(65) Prior Publication Data

US 2012/0271216 A1  Oct. 25, 2012

(51) Int. Cl.
  *A61F 13/00* (2006.01)
  *A61B 17/08* (2006.01)
  *A61B 17/68* (2006.01)

(52) U.S. Cl.
  CPC ............ *A61B 17/08* (2013.01); *A61B 17/685* (2013.01)

(58) Field of Classification Search
  CPC ........ A61B 17/08; A61B 17/685; A61F 13/00
  USPC .............. 602/57–59; 604/179–180; 128/888; 606/23–59, 151, 322, 329, 72
  See application file for complete search history.

(56) References Cited

U.S. PATENT DOCUMENTS

| | | | | |
|---|---|---|---|---|
| 3,683,911 | A | * | 8/1972 | McCormick ................... 604/180 |
| 4,291,698 | A | * | 9/1981 | Fuchs et al. ................... 606/232 |
| 4,519,793 | A | * | 5/1985 | Galindo ......................... 604/180 |
| 4,767,411 | A | * | 8/1988 | Edmunds ....................... 604/180 |
| 4,856,504 | A | * | 8/1989 | Yamamoto et al. ............. 606/59 |
| 4,915,694 | A | * | 4/1990 | Yamamoto et al. .......... 604/180 |
| 4,943,293 | A | * | 7/1990 | Lee, Jr. ............................ 606/96 |
| 5,080,661 | A | * | 1/1992 | Lavender et al. .............. 606/54 |
| 5,215,531 | A | * | 6/1993 | Maxson et al. ............... 604/180 |
| 5,263,939 | A | * | 11/1993 | Wortrich ........................ 604/174 |
| 5,360,020 | A | * | 11/1994 | Lee et al. ........................ 128/888 |
| 5,447,492 | A | * | 9/1995 | Cartmell et al. ................ 606/54 |
| 5,702,388 | A | * | 12/1997 | Jackson et al. ................. 606/54 |

(Continued)

*Primary Examiner* — Kim M Lewis
(74) *Attorney, Agent, or Firm* — Glenn E. Gold, P.A.; Glenn E. Gold

(57) ABSTRACT

A surgical pin compressive wound dressing housing is described as a device that couples with a wound dressing material or sponge of a specific type and provides a protective closed environment for the surgical point of entry wound where surgical pins or wires are applied. In addition, this device serves to stabilize such surgical pins or wires as they protrude from the surgically made pin site wound upon a patient's skin. Such pins or wires are often utilized, but not limited to, the fixation of fractured bones or when anatomic stabilization is needed. The unique cup like design of the wound dressing housing allows it to couple with a specific type of wound dressing material that has similar geometric features. The top of the wound dressing housing has a central pin hole whereby a pin stem extends upward. Together both the pin hole and pin stem receive the surgical pin or wire which can then be stabilized by the plastic closure snap in the front of the device after the wound dressing housing, and its corresponding wound dressing material, is pressed downward toward the surgical pin or wire point of entry wound. A hinge in the back of the device allows the wound dressing housing and its associated pin stem to split into equal right and left halves upon opening the device. This allows the device to be placed around the surgical pin or wire in question. By utilizing both the left and right hand clasps the user can close the device thus engaging the closure snap in the front of the wound dressing housing which secures the device in the closed position.

16 Claims, 3 Drawing Sheets

Legend

T - surgical pin trajectory

I - device / skin interface

S - skin

B - Bone

(56) References Cited

U.S. PATENT DOCUMENTS

| | | |
|---|---|---|
| 8,216,288 B2 | 7/2012 | Lee et al. |
| 2005/0049596 A1* | 3/2005 | Stewart ........................ 606/72 |
| 2006/0253089 A1* | 11/2006 | Lin ............................. 604/301 |

* cited by examiner

SURGICAL PIN COMPRESSION WOUND DRESSING DEVICE

BACKGROUND OF THE INVENTION

This invention shall be utilized in the field of surgery where surgical pins and or wires are utilized. Such surgical procedures are often performed to fixate fractured bones or to secure an anatomical stabilization device such as a halo or external fixator. Surgical pin or wire placement consists of inserting a portion of the surgical pin or wire through the patient's skin and into a bone while allowing a portion of the surgical pin or wire to extend outward from the patient's skin. The exposed pin or wire allows a fixation device to be attached. These surgical pins or wires must remain in position for some period of time depending on their intended purpose.

In the past other inventions such as patent numbers: U.S. Pat. Nos. 4,943,293 & 5,360,020 & 5,702,388 & provisional application No. 60/701,346 are designs that consist of collars, retainers or clips intended to stabilize a wound dressing or sponge in place over a surgical pin site. These devices are deficient in three main areas. First they lack symmetrical wound compression. Second they lack a closed wound dressing environment. Third they fail to provide sufficient stabilization of the surgical pin or wire. Adequate wound compression is directly related to the precise geometric coupling between the wound dressing and wound dressing stabilization device being used. These prior inventions lack a wound dressing housing and therefore provide asymmetric wound compression. Such asymmetry could lead to unequal skin tension and possible skin breakdown and soft tissue necrosis. Without a closed wound dressing environment drainage from the surgical pin or wire site will communicate with the patient's adjacent skin. This in turn can allow bacteria upon a patient's skin to track into the surgical pin or wire site causing a subsequent infection. Poor stabilization of a surgical pin or wire is first due the inability of collars, retainers or clips to maintain adequate pressure on the patient's skin. Due to a lack of rigidity, and the inherent pliability of wound dressing materials, most of the downward pressure needed to stabilize the surgical wire or pin is absorbed by the wound dressing or sponge. Second, the close proximity between the securing device of prior inventions (collars, retainers or clips) with the wound dressing material being used provides an inferior point of fixation.

Specific problems following the application of surgical fixation pins or wires is the aftercare relating to pin site wound dressings. Ordinary wound dressings lack wound compression, leading to excessive bleeding and drainage around the pin sites. Furthermore, the continuity of drainage soaked wound dressings with the patient's adjacent skin permits bacterial proliferation. Such proliferation allows bacteria from the skin outside the surgical pin or wire site to be channeled into the surgical pin or wire site. These circumstances set the stage for wound infections. In addition, the common method for changing and maintaining wound dressings around surgical pin sites is ineffective and laborious to say the least. Attempting to wrap sterile dressings around surgical pin sites does not provide adequate wound coverage or compression. For medical staff it is also a time consuming process resulting in decreased time to care for other patients. For the patient, lack of compliance because of the complexity of changing their surgical pin or wire site dressings at home results in leaving drainage soaked pin or wire site dressings on for days. These combined circumstances predispose the patient to wound infections. Furthermore, the high volume of disposable medical wound dressings used, and increased medical waste from daily dressing changes, will increase health care costs.

BRIEF SUMMARY OF THE INVENTION

The surgical pin compressive wound dressing housing is a biomedical mechanical device that allows for a compressive wound dressing to be applied and stabilized to the surgical pin or surgical wire sites of medical devices such as: halos, external traction pins and other such devices that utilize surgical wires or pins. This medical device shall be available in various forms, relating to different shapes and sizes, in order to custom fit a pre-manufactured wound dressing. The closed environment provided by the wound dressing housing will prevent wound drainage and help prevent against bacterial contamination. Unlike other known devices, the unique feature of this invention is the rigid non pliable wound dressing housing and pin hole and pin stem design and configuration. Together these components provide a means for applying wound compression to the wound site of a surgical pin site or wire while also stabilizing the surgical pin or wire. Structurally, the rigid nature of the wound dressing housing, as well as its precise fit as it couples with a specific wound dressing material, allows for symmetrical would compression. By providing a closed environment for the wound dressing material, the wound dressing housing acts to isolate the wound dressing and its corresponding wound drainage from the patient's adjacent skin. Furthermore, the pin hole and pin stem configuration allows for surgical pin or wire stability and variability with regards to the amount of wound compression desired. By having a well contoured pin hole and pin stem, in relation to the surgical pin or wire being used, the wound dressing housing maintains a proper position during its use. The importance of having a close fixation between the pin stem with the surgical pin or wire, and the wound dressing housing with the patient's skin, is that it will help prevent pin or wire movement during changes in patient positioning. The high center of gravity of the pin stem, along with the direct contact of the wide rigid base of the wound dressing housing with the patient's skin, provides for superior surgical pin or wire stabilization as compared to other inventions. The easy use and effectiveness of this device will enable medical staff to become more efficient and waste less time with laborious ineffective tasks such as time consuming wound dressing changes. Consequently, more time could be used for other patients resulting in an increase in the quality of patient care. For patients, at home wound dressing changes for those discharged from the hospital with surgical pins and or wires in place would be quite easily managed. The easy one handed use of this device allows all patient's, even those lacking formal experience with post surgical wound care methods, to properly care for their surgical wound sites. The decrease in both wound care supplies needed and medical waste generated, from the large quantity of discarded wound dressing bandages utilized, will ultimately cut health care costs.

DETAILED DESCRIPTION OF THE INVENTION

The present invention provides an effective, easy to use device that will stabilize a surgical orthopedic pin or wire utilized during medical procedures, while simultaneously providing a compressive wound dressing where such surgical pin or wire is introduced into the patient's skin. As the surgical pin or wire passes through the skin and into the bone, the pin or wire entry site, deeper soft tissues and the bone itself are prone to infection. Surgical pin or wire movement within the pin or wire entry site during patient movement is also a cause of tissue breakdown which can result in a higher incidence of infection. Furthermore, wound damage becomes another issue with regards to wound infections. Therefore, the protective action of a compressive wound dressing device, described hereinafter with reference to the drawings, will address these issues.

Figure 1:
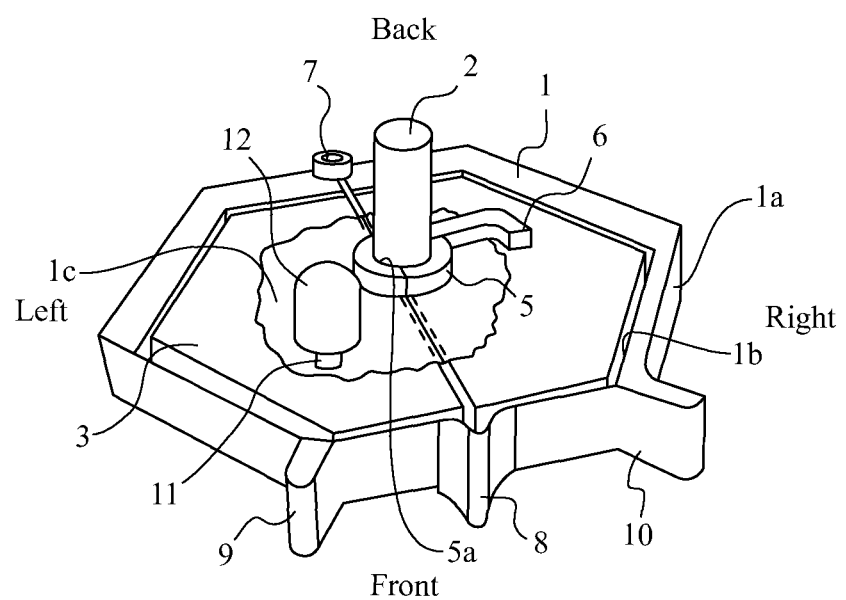
FIG. 1 Transparent view of the Surgical Pin Compressive Wound Dressing Housing in the closed position with associated wound dressing pad/sponge.
Figure 2:
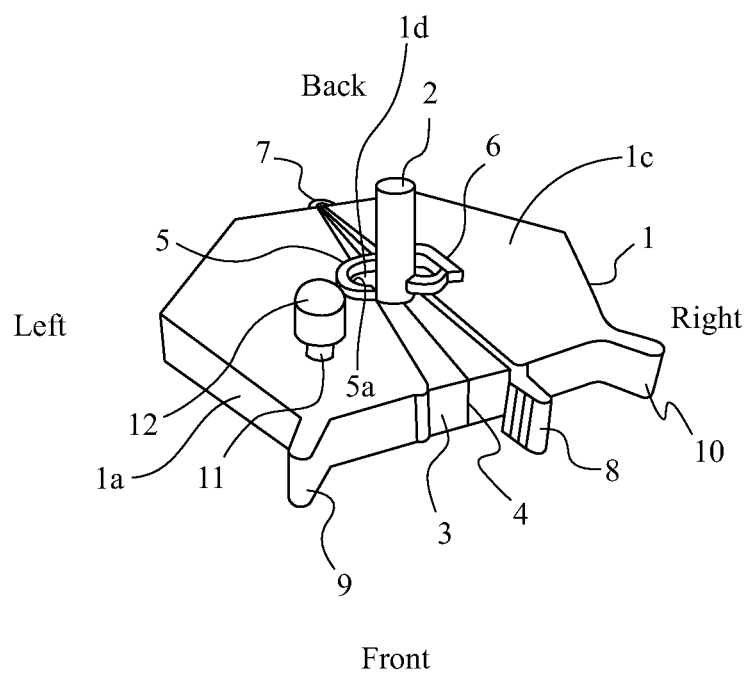
FIG. 2 Transparent view of the Surgical Pin Compressive Wound Dressing Housing in the open position with associated wound dressing pad/sponge.

(See FIGS. 1 & 2) The main component of this device is a wound dressing housing (1) that is specifically designed to provide a closed environment for a specific type of wound dressing being used. The housing (1) has a peripheral wall (1a) defining an interior cavity (1b) and an open bottom, and a cover (1c) connected on and extending across the peripheral wall (1a) so as to define a closed top of the interior cavity (1b), except for a hole (1d) centrally-defined in the cover (1c). Physically, the wound dressing housing resembles a rigid shallow inverted cup capable of receiving a wound dressing or surgical sponge. Functionally, the wound dressing housing (1) isolates the surgical wire or pin (2), and surgical wound site, from potential outside wound contaminants while also decreasing the amount of wound drainage. Furthermore, the design of the housing (1) will allow for a precise geometrical coupling with a specific type of wound dressing. A wound dressing material (3), of a pre-determined size, will be able to fit within the interior cavity (1b) of the wound dressing housing (1) of this device and have a hole or slit (4) to accommodate the passage of the surgical pin or wire (2). Typically the depth of the housing (1), and thus of its interior cavity (1b), is approximately ½ the width of the wound dressing material (3) being used. This quality gives the device the potential to provide wound compression.

Other components of the device include an annular stem (5), an opening stopper (6), a hinge (7), a closure snap (8), left and right hand clasps (9) and (10), a drainage port (11) and an associated drainage cap (12). The annular stem (5), that is attached on and extends upward from the cover (1c) at the top of the wound dressing housing (1), allows the surgical pin (2) to pass through the device. The actual space centralized within the annular stem (5) where the surgical pin or wire shall pass is referred to as the a pin passage 5(a). A precise fit between the annular stem (5) and the pin passage (5a) will correlate with the diameter of the surgical pin being utilized. The housing (1), and annular stem (5) therewith, are split diagonally into complementary parts, for instance equal halves, by a break extending between front and rear opposite locations on the peripheral wall (1a), diagonally entirely across the cover (1c), and through the hole (1d) and annular stem (5). The hinge (7), which is attached to and bridges the complementary parts of the housing (1) at the rear location thereon, allows the peripheral wall (1a) and cover (1c) of the housing (1), as well as the annular stem (5), to converted between closed and open positions around the surgical pin (2). The opening stopper (6), that extends from the annular stem (5), from a left to right position, prevents the wound dressing housing (1) from opening at the break beyond its functional capability. Upon opening the device the complementary parts of the wound dressing housing (1) and annular stem (5) thus separate into equal right and left halves, thus allowing the surgical pin (2) to enter centrally. The plastic closure snap (8) which is attached to and bridges the complementary parts of the housing (1) at the front location on the peripheral wall (1a) thereof, allows the housing, and annular stem therewith, to snap into the closed position after the device is set in place with various amounts of compressive variability thus allowing the user to alter the amount of wound compression for different wound care circumstances. Likewise, closure snap (8) can be unsnapped into an open position, as shown on FIG. 2 (i.e. the device can be toggled from an open to a closed configuration vis-à-vis the closure snap). Due to the precision from the geometrical correlation between both the wound dressing housing (1) and wound dressing material (3), as well as the close fit between the annular stem (5) and surgical pin or wire (2), an equal distribution of force is applied upon the wound dressing when the downward pressure is to the device.

Extending from the front of the device are both the left and right hand clasps (9) and (10) attached on the peripheral wall (1a) of the housing (1) spaced in opposite directions from the closure snap (8) to allow gripping by a user to assist in opening and closing the housing. These clasps are designed to allow the user to open and close the device with one hand. Extending from the top of the cover (1c) of the housing (1) of the device is the drainage port (11) to allow drainage from the interior cavity (1b) of the housing (1). The drainage port (11) is a small hollow tubular appendage capable of receiving plastic tubing that can be connected to a wound drainage system. This port is in direct continuity with the internal cavity (1b) of the wound dressing housing (1). The drainage port (11) has an associated plastic drainage cap (12) to be placed over the port when it is not in use.

This invention would be made from a clear plastic capable of providing this device with rigid, non-pliable, structural characteristics. A plastic molding process, from an outside manufacturer skilled in the craft, would be utilized to manufacture the invention. It wound be important to utilize a plastic material capable of withstanding conventional operating room sterilization techniques.

This invention has the potential for numerous modifications or versions of the aforementioned description. All the components are non-removable from the device with the exception of the cap for the wound drainage port. However, by interchanging the position of the parts in relationship to the geometric configuration of the device of the invention the device could operate the same. For example, by placing the hinge on the wound dressing housing on the opposite side in comparison with the original design would not change the overall functional capabilities of the device. Different versions of this device would entertain the possibility of utilizing different types of wound dressing materials. The adaptability of the device would be directly related to the geometric shape, depth and diameter of the wound dressing housing. For example a wound dressing housing having a hexagonal shape, as shown in the aforementioned diagrams, would be designed for one type of wound dressing material and a square wound dressing housing would be made to closely contour another type of wound dressing material. These versions would consist of wound dressing housings having different geometric attributes that would coincide with the wound dressing material being used. Other modifications would be made in accordance with the working distance of two or more devices that are used simultaneously. The working distance of the device, or the distance at which two devices can be placed side by side without interfering with one another, is directly related to the proximity of two adjacent surgical pins or wires. Alterations with cover hole and annular stem placement, in relation to the wound dressing housing, would be included to accommodate those situations when two or more surgical pins must be used together within close proximity of one another. Furthermore, variations of cover hole and annular stem diameters and lengths would be considered in designs that call for different sizes of surgical pins or wires.

Figure 3:
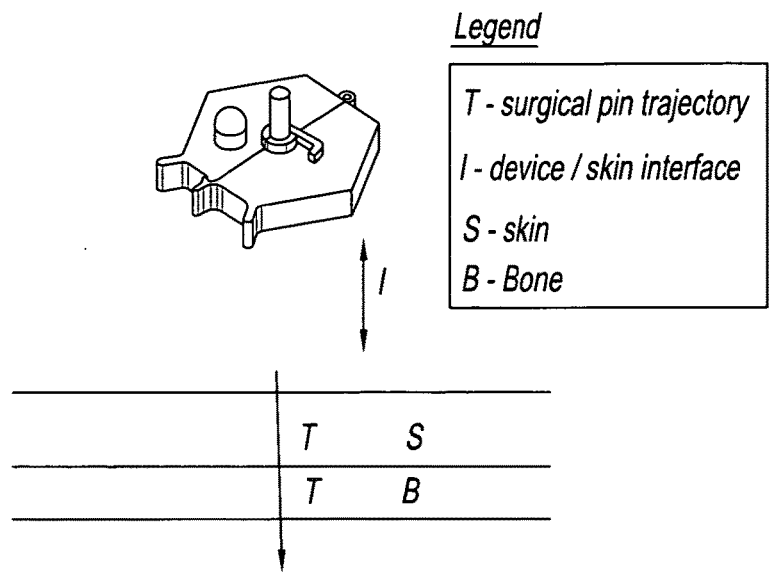
FIG. 3 Non-transparent view of the Surgical Pin Compressive Wound Dressing Housing in the closed position with associated wound dressing pad/sponge sitting atop the patient's skin and associated bone.
Figure 4:
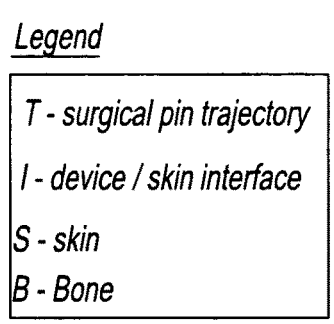
FIG. 4 Non-transparent view of the Surgical Pin Compressive Wound Dressing Housing in the open position with associated wound dressing pad/sponge sitting atop the patient's skin and associated bone.
Figure 4:
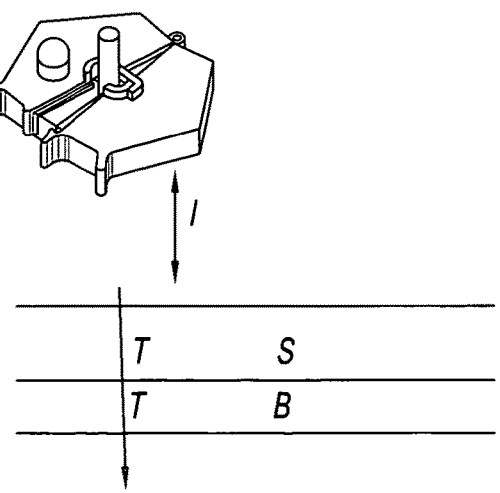

(See FIGS. 3 & 4) Using this invention is quite easy. First, a wound dressing material of a predetermined size will be placed over the surgical wire or pin site wound in question (over the patient's skin). Next sterile a gauze, or prefabricated rubber seal, with a horizontal slit made from its peripheral edge to the center (to allow passage of the surgical pin), is placed over the wound dressing material. Then the wound dressing housing of the device is opened, slipped around the surgical pin and then closed. Following that the user will press the device downward (toward the pin site wound upon the patient's skin) until the wound dressing housing couples with wound dressing material and articulates with the patient's skin. At this point the sterile gauze or prefabricated seal provides a cushion between the bottom of the wound dressing housing and the patient's skin. The amount of downward pressure will determine the degree of wound compression exerted upon the patient. Finally, when the desired wound compression is achieved, the user closes the device using the left and right hand clasps until the front closure snap is engaged. This secures the device to the surgical pin or wire. Wound dressing changes are easily performed by the health care provider or the patient by repeating the process mentioned above while changing both the wound dressing material as well as the sterile gauze.

The invention claimed is:

1. A surgical pin compressive wound dressing device comprising:
   a wound dressing housing, including
     a peripheral wall defining an interior cavity and an open bottom, and
     a cover connected to and extending across said peripheral wall so as to define a closed top of said interior cavity, said cover spaced from said open bottom such that said housing has a shallow inverted cup-shaped configuration allowing said housing to overlie a wound site with said open bottom of said peripheral wall facing toward the wound site and said interior cavity enclosing and retaining in a state of compression a wound dressing material overlying and contacting the wound site, a hole centrally-defined in said cover of said housing so as to allow a surgical orthopedic pin, protruding outward from the wound site and through the wound dressing material, to pass through said cover to extend above said housing;
   an annular stem attached to and extending upward from said cover of said housing about said hole in said cover of said housing, said annular stem having a passage therethrough aligned with said hole in said cover so as to allow said passage of said annular stem to receive and stabilize the surgical orthopedic pin as it passes through said passage, wherein said housing, and said annular stem therewith, are split diagonally into complementary parts by a break extending between first and second opposite locations on said peripheral wall, diagonally entirely across said cover, and through said hole and said annular stem;
   a hinge attached to and bridging said complementary parts of said housing at said first of said opposite locations on said peripheral wall of said housing so as to enable said housing, and said annular stem therewith, to convert between open and closed positions around the surgical orthopedic pin; and
   a closure attached to and bridging said complementary parts of said housing at said second of said opposite locations on said peripheral wall of said housing and being operable to retain said housing, and said annular stem therewith, in said closed position around the surgical orthopedic pin and at a predetermined position along the surgical orthopedic pin so as to stabilize the surgical orthopedic pin and retain the wound dressing material in said state of compression against the wound site.

2. The device as recited in claim 1, wherein said wound dressing housing and said annular stem are made of rigid non-pliable material.

3. The device as recited in claim 1, further comprising a pair of left and right hand clasps attached on said peripheral wall of said housing spaced in opposite directions from said closure to allow gripping by a user to assist in opening and closing of said housing.

4. The device as recited in claim 1, further comprising an opening stopper attached to one of said housing and said annular stem and adapted to limit the distance of separation between said complementary parts of said housing when in said open condition.

5. The device as recited in claim 1, further comprising a drainage port on said housing to allow from drainage from said interior cavity of said housing.

6. The device as recited in claim 5, further comprising a cap adapted to be removed from and placed upon said drainage port.

7. The device as recited in claim 5, wherein said drainage port is on said cover of said housing.

8. A surgical pin compressive wound dressing device comprising:
   a wound dressing housing, including
     a peripheral wall defining an interior cavity and an open bottom, and
     a cover connected to and extending across said peripheral wall so as to define a closed top of said interior cavity, said cover spaced from said open bottom such that said housing has a shallow inverted cup-shaped configuration allowing said housing to overlie a wound site with said open bottom of said peripheral wall facing toward the wound site and said interior cavity enclosing and retaining in a state of compression a wound dressing material overlying and contacting the wound site, a hole centrally-defined in said cover of said housing so as to allow a surgical orthopedic pin, protruding outward from the wound site and through the wound dressing material, to pass through said cover to extend above said housing;

an annular stem attached to and extending upward from said cover of said housing about said hole in said cover of said housing, said annular stem having a passage therethrough aligned with said hole in said cover so as to allow said passage of said annular stem to receive and stabilize the surgical orthopedic pin as it passes through said passage, wherein said housing, and said annular stem therewith, are split diagonally into complementary parts by a break extending between first and second opposite locations on said peripheral wall, diagonally entirely across said cover, and through said hole and said annular stem;

a hinge attached to and bridging said complementary parts of said housing at said first of said opposite locations on said peripheral wall of said housing so as to enable said housing, and said annular stem therewith, to convert between open and closed positions around the surgical orthopedic pin;

a closure attached to and bridging said complementary parts of said housing at said second of said opposite locations on said peripheral wall of said housing and being operable to retain said housing, and said annular stem therewith, in said closed position around the surgical orthopedic pin and at a predetermined position along the surgical orthopedic pin so as to stabilize the surgical orthopedic pin and retain the wound dressing material in said state of compression against the wound site;

a pair of left and right hand clasps attached to said peripheral wall of said housing spaced in opposite directions from said closure to allow gripping by a user to assist in opening and closing of said housing;

an opening stopper attached to one of said housing and said annular stem and adapted to limit the distance of separation between said complementary parts of said housing when in said open condition; and a drainage port on said housing to allow from drainage from said interior cavity of said housing, said port having a cap adapted to be removed therefrom and placed thereon.

9. A surgical pin compressive wound dressing device, comprising:

a wound dressing material adapted to overlie and contact a wound site having a surgical orthopedic pin protruding outward therefrom, through and extending above said wound dressing material;

a wound dressing housing, including
  a peripheral wall defining an interior cavity and an open bottom, and
  a cover connected to and extending across said peripheral wall so as to define a closed top of said interior cavity, said cover spaced from said open bottom such that said housing has a shallow inverted cup-shaped configuration allowing said housing to overlie the wound site with said open bottom of said peripheral wall facing toward the wound site and said interior cavity enclosing and retaining in a state of compression said wound dressing material overlying and contacting the wound site, a hole centrally-defined in said cover of said housing so as to allow the surgical orthopedic pin, protruding outward from the wound site and through said wound dressing material, to pass through said cover to extend above said housing;

an annular stem attached to and extending upward from said cover of said housing about said hole in said cover of said housing, said annular stem having a passage therethrough aligned with said hole in said cover so as to allow said passage of said annular stem to receive and stabilize the surgical orthopedic pin as it passes through said passage, wherein said housing, and said annular stem therewith, are split diagonally into complementary parts by a break extending between first and second opposite locations on said peripheral wall, diagonally entirely across said cover, and through said hole and said annular stem;

a hinge attached to and bridging said complementary parts of said housing at said first of said opposite locations on said peripheral wall of said housing so as to enable said housing, and said annular stem therewith, to convert between open and closed positions around the surgical orthopedic pin; and a closure attached to and bridging said complementary parts of said housing at said second of said opposite locations on said peripheral wall of said housing and being operable to retain said housing, and said annular stem therewith, in said closed position around the surgical orthopedic pin and at a predetermined position along the surgical orthopedic pin so as to stabilize the surgical orthopedic pin and retain said wound dressing material in said state of compression against the wound site.

10. The device as recited in claim 9, wherein said wound dressing housing and said annular stem are made of rigid non-pliable material.

11. The device as recited in claim 9, further comprising a pair of left and right hand clasps attached on said peripheral wall of said housing spaced in opposite directions from said closure to allow gripping by a user to assist in opening and closing of said housing.

12. The device as recited in claim 9, further comprising an opening stopper attached to one of said housing and said annular stem and adapted to limit the distance of separation between said complementary parts of said housing when in said open condition.

13. The device as recited in claim 9, further comprising a drainage port on said housing to allow from drainage from said interior cavity of said housing.

14. The device as recited in claim 13, further comprising a cap adapted to be removed from and placed upon said drainage port.

15. The device as recited in claim 13, wherein said drainage port is on said cover of said housing.

16. The device as recited in claim 9, wherein said wound dressing material has a geometric configuration matching that of said interior cavity of said wound dressing housing.

* * * * *